US010124156B2

(12) United States Patent
Johnson et al.

(10) Patent No.: US 10,124,156 B2
(45) Date of Patent: *Nov. 13, 2018

(54) SURGICAL ACCESS PORT AND METHOD OF USING SAME (71) Applicant: Applied Medical Resources Corporation, Rancho Santa Margarita, CA (US)

(72) Inventors: Gary M. Johnson, Rancho Santa Margarita, CA (US); John R. Brustad, Rancho Santa Margarita, CA (US); Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/269,529

(22) Filed: May 5, 2014

(65) Prior Publication Data

US 2014/0243869 A1    Aug. 28, 2014

Related U.S. Application Data (63) Continuation of application No. 13/209,200, filed on Aug. 12, 2011, now Pat. No. 8,715,251, which is a (Continued)

(51) Int. Cl.
*A61M 25/00*  (2006.01)
*A61M 39/02*  (2006.01)
(Continued)

(52) U.S. Cl.
CPC .............. *A61M 39/02* (2013.01); *A61B 17/34* (2013.01); *A61B 17/3417* (2013.01);
(Continued)

(58) Field of Classification Search
CPC .................... A61B 17/3417; A61B 2017/3456
See application file for complete search history.

(56) References Cited

U.S. PATENT DOCUMENTS 3,674,014 A    7/1972  Tillander
5,042,475 A    8/1991  LaBombard
(Continued)

OTHER PUBLICATIONS

U.S. Appl. No. 10/489,403, filed Mar. 11, 2004; Title: Bladeless Obturator and associated File History.
(Continued)

*Primary Examiner* — Deanna K Hall
(74) *Attorney, Agent, or Firm* — John F. Heal (57) ABSTRACT A surgical access port for insertion into a body cavity can have an elongate tubular body extending along an axis between a proximal end and a distal end, and a tip at the distal end of the tubular body for penetrating through a body wall and into the body cavity. The distal tip moves from a first, penetrating position to a second, retaining position when the body wall has been traversed. The surgical access port may further comprise a seal housing connected to the proximal end of the tubular body, the seal housing having an access port providing an opening into the tubular body to allow passage of surgical instruments. The distal tip may be sharp, pointed or bladed. The distal tip may also be substantially blunt or have a conical surface. The access port may further comprise a retention member for connecting the tubular body and the distal tip.

16 Claims, 8 Drawing Sheets

Related U.S. Application Data continuation of application No. 10/805,864, filed on Mar. 22, 2004, now Pat. No. 8,007,477.

(51) Int. Cl.
*A61B 17/34* (2006.01)
*A61B 17/00* (2006.01)

(52) U.S. Cl.
CPC ........... *A61B 2017/00473* (2013.01); *A61B 2017/3482* (2013.01); *A61B 2017/3484* (2013.01)

(56) References Cited

U.S. PATENT DOCUMENTS

| | | |
|---|---|---|
| 5,147,376 A | 9/1992 | Pianetti |
| 5,158,552 A | 10/1992 | Borgia et al. |
| 5,279,564 A | 1/1994 | Taylor et al. |
| 5,279,575 A * | 1/1994 | Sugarbaker ........ A61B 17/3403 604/104 |
| 5,342,382 A | 8/1994 | Brinkerhoff |
| 5,354,302 A | 10/1994 | Ko |
| 5,372,588 A | 12/1994 | Farley |
| 5,429,598 A | 7/1995 | Waxman |
| 5,707,362 A * | 1/1998 | Yoon ................ A61B 17/3417 604/164.03 |
| 5,971,960 A * | 10/1999 | Flom ................ A61B 17/3417 604/167.01 |
| 6,027,518 A | 2/2000 | Gaber et al. |
| 7,686,823 B2 | 3/2010 | Pingleton et al. |
| 7,708,713 B2 | 5/2010 | Albrecht et al. |
| 7,758,603 B2 | 7/2010 | Taylor et al. |
| 7,947,058 B2 | 5/2011 | Kahle et al. |
| 2001/0037128 A1 | 11/2001 | Arambula |
| 2001/0049493 A1 | 12/2001 | Lyon |
| 2007/0282365 A1* | 12/2007 | Popov ................ A61B 17/3417 606/192 |
| 2014/0243869 A1* | 8/2014 | Johnson ............ A61B 17/3417 606/185 |

OTHER PUBLICATIONS

U.S. Appl. No. 10/956,167, filed Oct. 1, 2004; Title: Bladeless Optical Obturator and associated File History.
U.S. Appl. No. 11/170,567, filed Jun. 29, 2005; Title: Insufflating Optical Surgical Instrument and associated File History.
U.S. Appl. No. 10/745,262, filed Dec. 23, 2003; Title: Catheter With Conduit Traversing Tip and associated File History.
U.S. Appl. No. 11/868,883, filed Oct. 8, 2007; Title: Visual Insufflation Port and associated File History.
U.S. Appl. No. 10/514,313, filed Nov. 12, 2004; Title: Blunt Tip Obturator and associated File History.

* cited by examiner

SURGICAL ACCESS PORT AND METHOD OF USING SAME

CROSS-REFERENCE TO RELATED APPLICATIONS

This application is a continuation of U.S. patent application Ser. No. 13/209,200, entitled "SURGICAL ACCESS PORT AND METHOD OF USING SAME," filed on Aug. 12, 2011, currently pending, which is a continuation of U.S. patent application Ser. No. 10/805,864, entitled "SURGICAL ACCESS PORT AND METHOD OF USING SAME," filed on Mar. 22, 2004, issued as U.S. Pat. No. 8,007,477. The entireties of each of these related applications are fully incorporated herein by reference.

BACKGROUND OF THE INVENTION

Field of the Invention

This invention generally relates to surgical access systems and, in particular, to a surgical access port having an integral penetrating distal tip and method of using same.

Discussion of the Prior Art

Laparoscopic surgery typically requires an access device such as a trocar. The term trocar generally refers to a combination of cooperating elements such as a cannula, a seal housing and an obturator. The cannula defines a pathway through a body wall; the seal housing provides an isolation of that pathway; and the obturator cuts or pierces the body wall so that the cannula may be inserted. All three components are usually fitted together and used as a single unit for passage through the body wall and into a body cavity. Once the body cavity, or potential body cavity is reached with the trocar, the obturator is removed and the cannula and seal housing are used as a passageway into the body cavity.

Laparoscopic surgery can be initiated as follows: first, a large bore needle is passed through a body wall and into the internal region associated with the body wall. Next, an inflation or insufflation gas is pumped into the internal region until it is properly distended. The body wall and internal region are now ready for insertion of trocars.

A common method for inserting a trocar system through a body wall is as follows: first, a small skin incision about the length of the diameter of the cannula is made. Second, the obturator and cannula are pushed into the skin incision and are continually pushed until the system has passed through the body wall and into the interior region associated with the body wall. Third, the obturator is removed from the trocar system. The cannula and seal housing are now ready for use.

Placing a sharp instrument such as an inflation needle or trocar obturator through a body wall and into an associated internal region comes with considerable risk. The human abdomen, for example, is a tightly packed region that is filled with delicate structures and organs. There is no open space between the abdominal wall and those structures or organs until inflation gas is inserted and a pneumoperitoneum is established. Great care must be taken when placing inflation needles so as to avoid penetration of intestine, bowel or other structures. Most inflation/insufflation needles have a safety mechanism associated with the sharp end of the needle. Generally it is a spring loaded, blunted core that extends after the tip of the needle has passed through the body wall. There remains, however, a constant risk associated with the spring mechanism since the sharp needle tip extends beyond the safety core during the entire insertion process and somewhat beyond.

Even after pneumoperitoneum is established, there is a risk of injury during placement of additional sharp instruments through the distended body wall. The body wall is comprised of skin, muscle, fat and a thin membrane. The wall may be thick, muscular and tough or it may be lean and soft. As such, placement of a sharp obturator through the body wall requires great skill and knowledge of what lies within the internal region. The force required to insert a sharp trocar through a body wall can exceed forty pounds in some cases. This applied force easily overcomes the pneumoperitoneum and forces the body wall down and against delicate structures where there is the danger of piercing or cutting those structures.

This is not a new problem. Over the years there have been many solutions proposed. The shielded obturators have spring loaded or spring driven safety components that either cover the sharp portions of the obturator or retract the sharp components within the obturator shaft. These mechanisms are complex, costly and not without risk. Many surgeons have also used a technique referred to as a "cut down" procedure where successive small incisions are made until the body wall is cut through, at which time a cannula is inserted. Many feel that this procedure is safe but it is time-consuming and still has some associated risk since it continues to make use of a sharp instrument during the entire passage through the body wall. A sequential dilating system is another device that some surgeons use. This system comprises a sharp needle and associated composite sleeve that are placed into the abdomen followed by a blunted obturator. This system continues to require insertion of a sharp needle followed by the forceful placement of an obturator.

In all of the above prior art systems, the laparoscopic procedures begin with the insertion of a sharp instrument at a nearly perpendicular angle to the body wall and followed by placement of the trocars with a forceful passage of either a sharp or blunted obturator through the body wall. As explained above, a drawback of these systems is that the danger of piercing or cutting internal structures still remains.

Accordingly, there is a need in the art for a system that minimizes the risk associated with insertion of the trocar cannula while allowing the use of the most efficient penetrating profile.

SUMMARY OF THE INVENTION

The present invention relates to a surgical access port for insertion into a body cavity having an elongate tubular body extending along an axis between a proximal end and a distal end, and a tip disposed at the distal end of the tubular body for penetrating through a body wall and into the body cavity. The distal tip operates to move from a first, penetrating position to a second, retaining position when the body wall has been traversed. As such, there is no need for a separate obturator to be used with the access port of the invention. Furthermore, the distal tip can act as an anchor to prevent accidental removal of the tubular body. The surgical access port may further comprise a seal housing operably connected to the proximal end of the tubular body, the seal housing having an access port providing an opening into the tubular body to allow passage of surgical instruments. The distal tip may be sharp, pointed or bladed. The distal tip may also be substantially blunt or have a conical surface. The access port may further comprise a retention member for connecting the tubular body and the distal tip. The retention member may be formed from metal or plastic, which may be operably connected with a sidewall of the tubular body. The retention member may be biased to hold the distal tip in an off-axis position when there is no axial load, or it may be lightly held in axial alignment and subsequently deflected in the presence of an instrument within the tubular body. The retention member may be one of a spring, spring wire, offset hinge or "living" hinge.

In one aspect of the invention, the distal tip repositions to one side of the tubular body in a substantially right-angled condition in the second, retaining position. The distal tip may also reposition to one side of the tubular body when no axial load is present to hold it in axial alignment with the tubular body. It is appreciated that the repositioned tip remains in an off-axis condition until removal of the access port, at which time the distal tip automatically realigns with the axis of the tubular body as the access port is withdrawn from the body wall. The distal tip may also comprise at least two or more parts or petals that reposition to the side of the tubular body in the second, retaining position. The tubular body may be a thin walled tube sized and configured to allow passage of surgical instruments through the body wall and into the body cavity. The distal tip may comprise a conical, tapered or rounded shape to separate tissue layers and to provide a small fascial defect through which the tubular body can pass. The distal tip may be solid or hollow. The hollow distal tip may act as a specimen bag by closing on a specimen and pulled inside the tip during removal of the access port.

The distal tip may be formed from a clear material to allow viewing through an endoscope during placement of the surgical access port. The conical surface of the tip may have at least one tissue engaging raised pattern on the surface. The conical surface operates to facilitate insertion of the access port with a reduced penetration force and minimize tenting of the body wall. The conical surface may further facilitate separation of different layers of the body wall and provides proper alignment of the tip between the layers. In another aspect of the invention, the distal tip may have an outer surface extending distally to a blunt point and includes a pair of side sections separated by an intermediate section, and wherein the side sections extend from the blunt point radially outwardly with progressive positions proximally along the axis. The side sections may include a distal portion in proximity to the blunt point and a proximal portion in proximity to the tubular body, and the distal portion of the side sections being twisted radially with respect to the proximal portion of the side sections.

In yet another aspect of the invention, a method of inserting a surgical access port into a body cavity is disclosed. The method comprises the steps of: providing the surgical access port having an elongate tubular body extending along an axis between a proximal end and a distal end, and a distal tip operably connected at the distal end of the tubular body; and inserting and advancing the distal tip through a body wall and into the body cavity. The method may further comprise the step of making a small skin incision with the distal tip. A feature of the invention is that the distal tip moves from a first, penetrating position to a second, retaining position when the body wall has been traversed without a need for a separate obturator. The method of the invention further comprises the step of removing the access port from the body cavity after a procedure is complete. It should be noted that during the removal of the access port, the distal tip, which may comprise of one or more part or petal, automatically realigns with the axis of the tubular body as the access port is withdrawn from the body wall.

These and other features and advantages of the invention will become more apparent with a discussion of preferred embodiments in reference to the associated drawings.

DESCRIPTION OF PREFERRED EMBODIMENTS AND BEST MODE OF THE INVENTION

Figure 1:
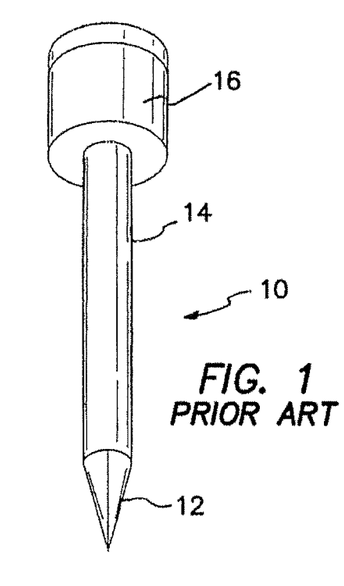
FIG. 1 illustrates a conventional laparoscopic access port having a cutting tip.
Figure 2:
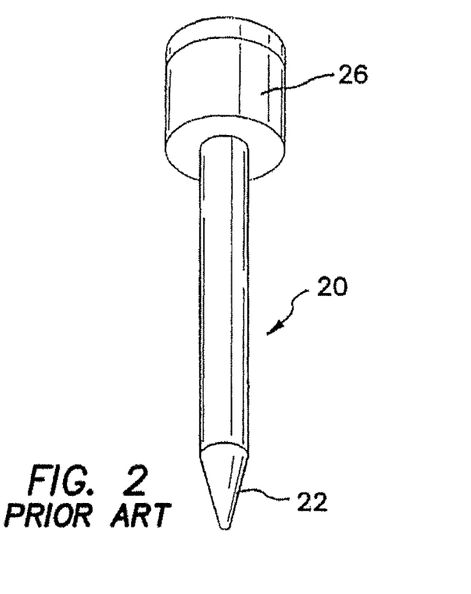
FIG. 2 illustrates a conventional laparoscopic access port having a blunt tip.
Figure 3:
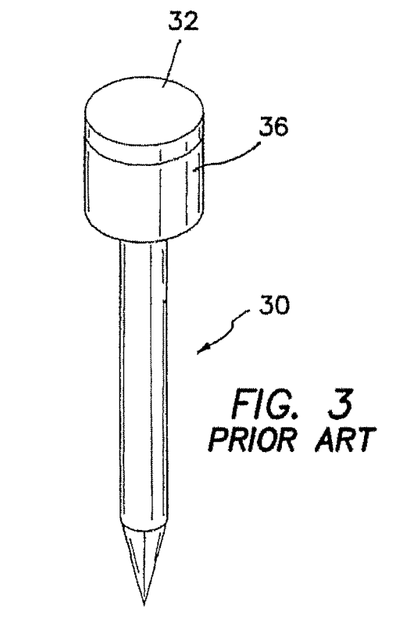
FIG. 3 is a top-perspective view of the conventional laparoscopic access port of FIG. 1 showing the proximal position of an obturator handle.

Referring to FIGS. 1-3, there are shown conventional laparoscopic access port systems of the prior art. In particular, FIG. 1 illustrates a conventional laparoscopic access port system 10 having a cuffing tip 12. FIG. 2 illustrates a conventional laparoscopic access port system 20 having a blunt tip 22; and FIG. 3 illustrates a top-perspective view of a conventional laparoscopic access port system 30 showing a proximal position of an obturator handle 32. In each of the above conventional laparoscopic access port systems 10, 20, 30, there are included a cannula or elongate tubular body 14, 24, 34, a seal housing 16, 26, 36, respectively, and an obturator (not shown). The cannula 14, 24, 34 for the respective access port system 10, 20, 30 provides a tubular pathway through a body wall. The seal housing 16, 26, 36 provides isolation between the two sides of the body wall. The obturator provides a cutting or dilating instrument for placing the cannula through the body wall. The three combined elements of the access port system—cannula, seal housing and obturator—are generally referred to as a "trocar".

Figure 4:
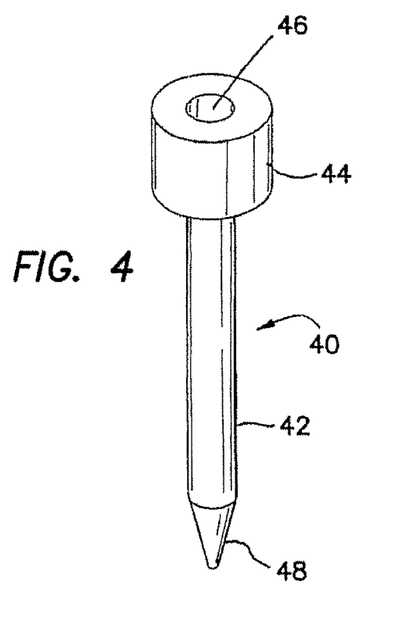
FIG. 4 is a top-perspective view of a laparoscopic access port according to the first embodiment of the invention showing the seal housing with no obturator in place.

Referring to FIG. 4, there is shown a top-perspective view of a laparoscopic access port 40 according to the first embodiment of the invention. The access port 40 includes a cannula or elongate tubular body 42 having a proximal end and a distal end, a seal housing 44 operably connected at the proximal end of the cannula 42, and an access port 46 formed in the seal housing 44. A feature of the invention is it contemplates the use of the access port system 40 without the need for an obturator. An advantage of the invention is it simplifies the insertion of an access port through a body wall. In particular, with the access port 40 of the invention, at least the following steps of operating the conventional access port systems of the prior art will be eliminated: (1) placing an obturator into an access port; (2) holding the obturator in place during placement of the access port; (3) subsequently removing the obturator when access is complete; and (4) disposal of the obturator. The distal end of the cannula 42 comprises a tip 48 that is sized and configured to guide the tubular portion of the cannula 42 through a body wall. Distal tip 48 may be sharp, pointed or bladed. In one aspect of the invention, the tip 48 comprises a substantially blunt or rounded frusto conical structure having at least one tissue engaging helical raised pattern upon the conical surface.

Figures 5, 6, 7, 8:
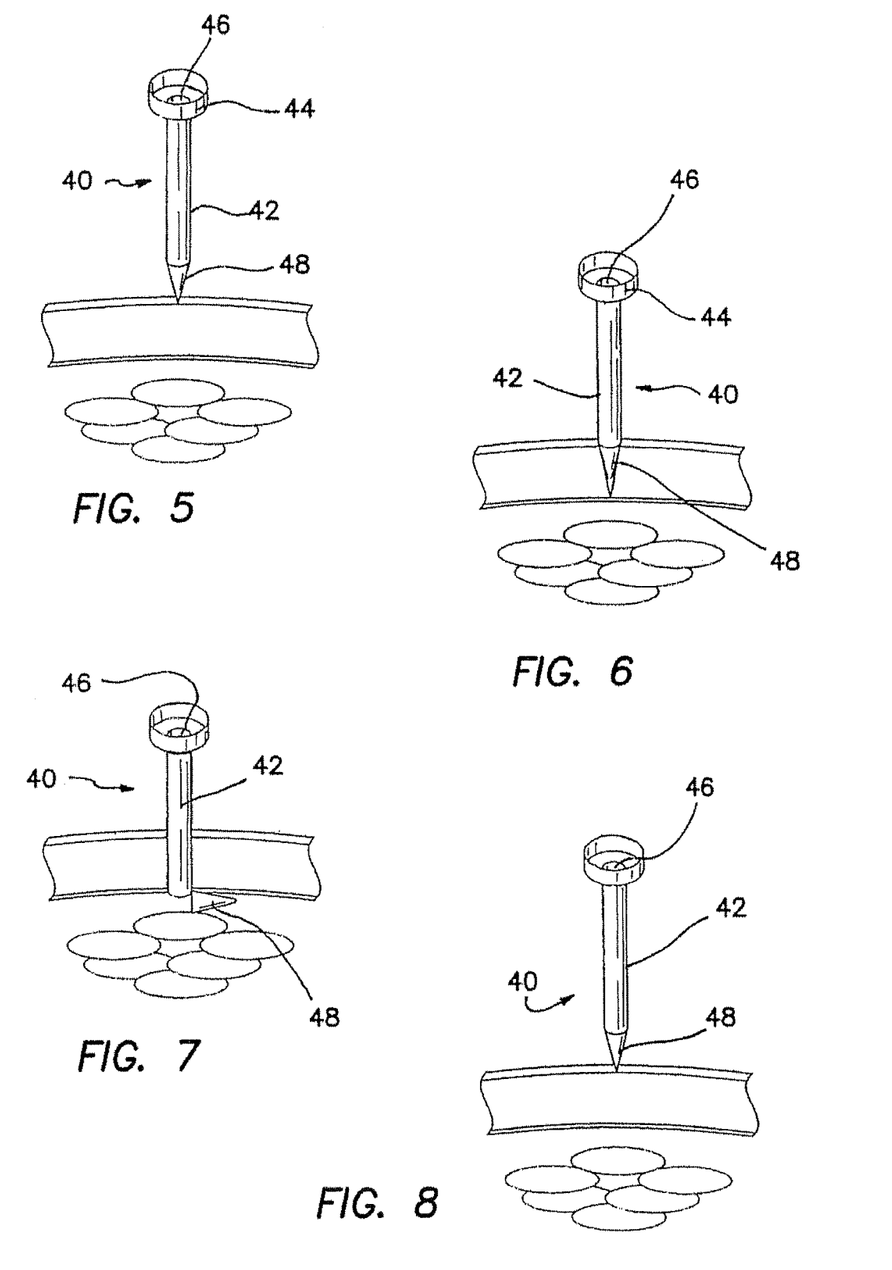
FIG. 5 illustrates the first step in placing the access port of the invention through a body wall.
FIG. 6 illustrates the second step in placing the access port of the invention through a body wall.
FIG. 7 illustrates the third step in placing the access port of the invention through a body wall.
FIG. 8 illustrates the removal step for removing the access port of the invention through a body wall.
Figure 9:
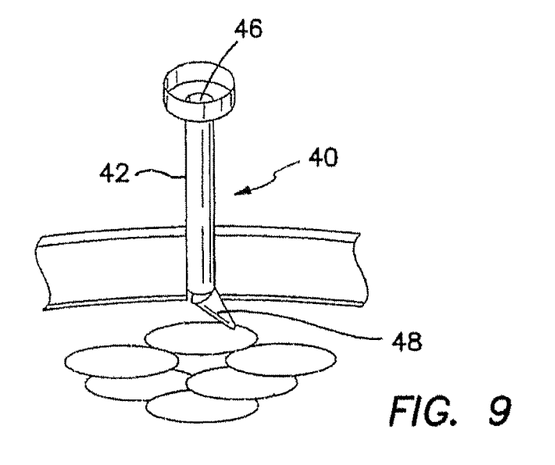
FIG. 9 is an enlarged view of the initiation of the removal step of FIG. 8.
Figure 10:
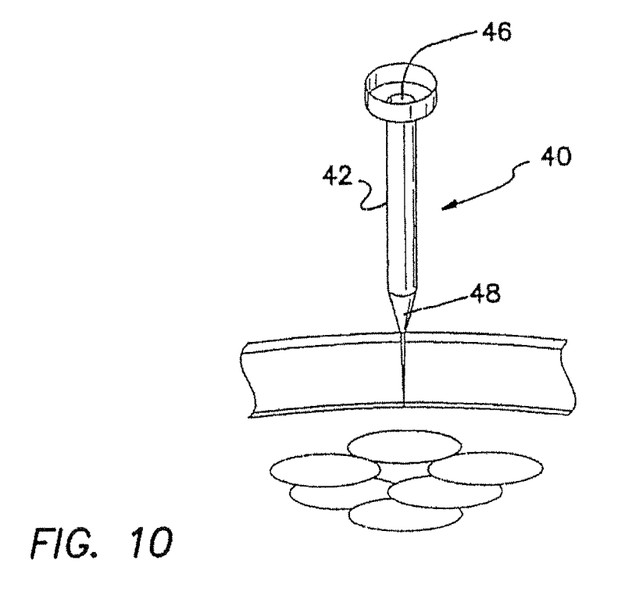
FIG. 10 is an enlarged view of the completed removal step of FIG. 8.
Figures 11, 12:
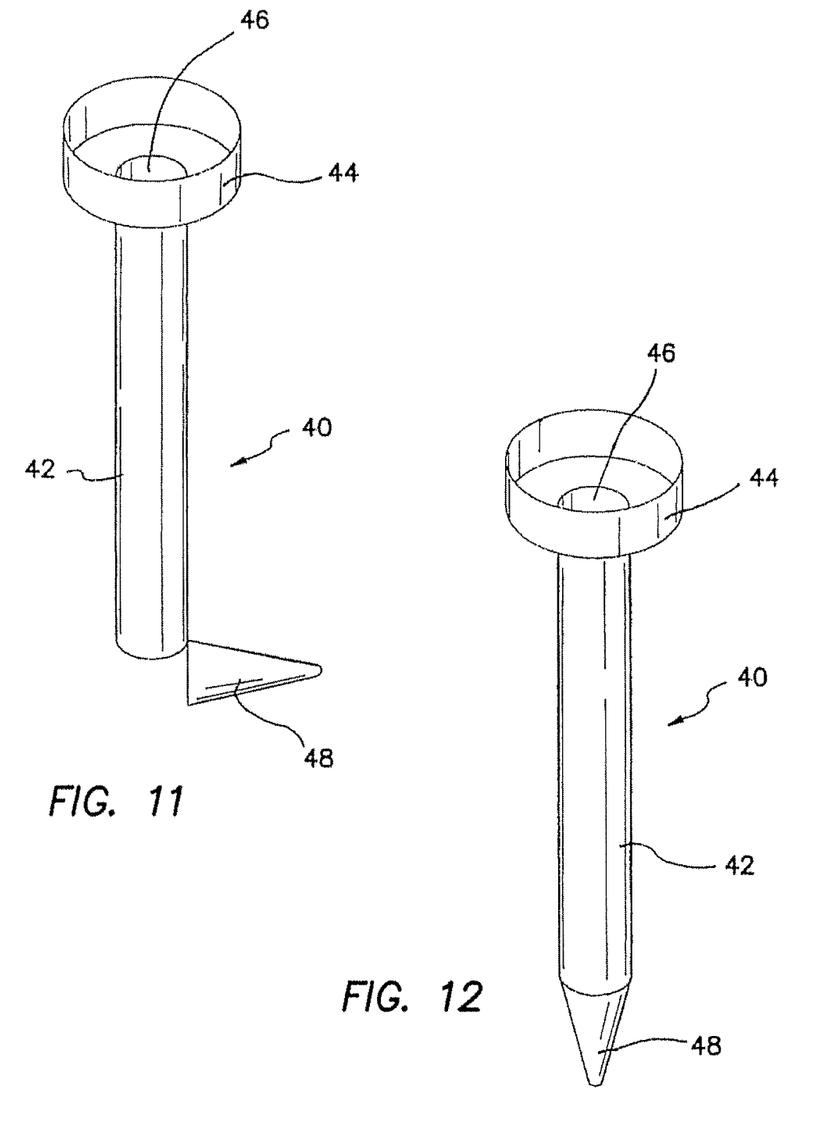
FIG. 11 is a schematic view of the distal cannula portion in a retention position.
FIG. 12 is a schematic view of the distal cannula portion in an insertion or removal position.

Referring to FIGS. 5-10, there is shown a method of inserting the surgical access port of the present invention and, in particular, there are shown a series of illustrations of the surgical access port in use to provide access through a body wall and into an internal portion of a body. First, an entry is initiated by a small skin incision as illustrated in FIG. 5, followed by insertion of the distal portion of the access port 42 as illustrated in FIG. 6. The access port 40 is advanced into the fascial defect until the innermost layer of tissue is penetrated. When the distal portion of the access port 40 passes through the final layer of tissue, it repositions itself to one side of the cannula 42 as illustrated in FIG. 7. The repositioned distal tip 48 remains in a substantially right-angled, off-axis, condition until removal of the access port. The distal tip 48 automatically realigns with the axis of the cannula 42 as the access port is withdrawn from the body wall as illustrated in FIG. 8. FIGS. 9 and 10 are enlarged views of the initiation and completion of the removal step of FIG. 8.

Stated another way, the present invention contemplates the use of a distal portion that separates body tissue rather than cutting the tissue. The resulting residual defect is minimal and easily corrected. In addition, the blunt or rounded configuration of the distal tip allows it to remain in the angled, off-axis condition during use since there are no sharp, pointed or cutting elements associated with the distal portion.

Figures 20A, 20B, 20C:
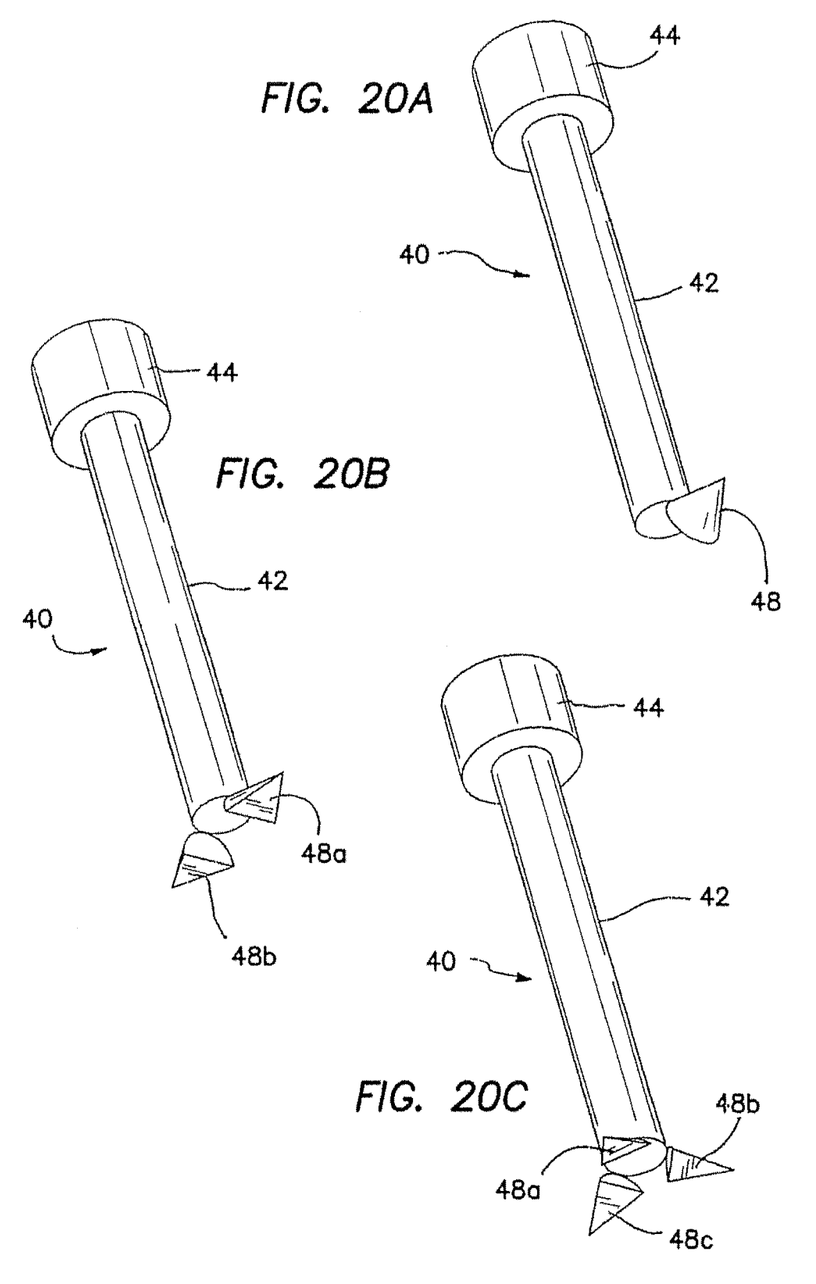
FIGS. 20(a)-20(c) illustrate perspective views of an access port having a single-piece distal tip, a two-piece distal tip and a three-piece distal tip, respectively.

FIGS. 11-16 illustrate the details of the construction of access port 40 according to the present invention. In particular, access port 40 comprises a cannula or elongate tubular body 42 having a proximal end and a distal end, seal housing 44 operably connected at the proximal end, and tip 48 disposed at the distal end. Cannula 42 is formed from a very thin walled tube that is sized and configured to allow passage of surgical instruments through a body wall and into a body cavity. The distal tip 48 may be solid or hollow. The hollow tip may act as a specimen bag by closing on a specimen and pulled inside the tip during removal of the access port. The tip 48 is sized and configured to facilitate the placement of the tubular cannula 42. The tip 48 comprises conical, tapered or rounded shape that separates tissue layers and provides a small fascial defect through which the associated cannula 42 may pass. A metal or plastic retention member 47 is associated with the sidewall of the cannula tube and extends into the distal tip 48. The distal tip 48 may swing to one side when no axial load is present to hold it in axial alignment with the cannula tube. The retention member 47 may be biased to hold the distal tip 48 in an off-axis position when there is no axial load or the tip 48 may be lightly held in axial alignment and subsequently deflected in the presence of instruments within the cannula 42. FIGS. 20(a)-20(c) illustrate perspective views of a single-piece 48(a), a two-piece 48(a)/48(b) and a three-piece 48(a)/48(b)/48(c) distal tip, respectively, that may swing to the side of the tubular cannula 42 when no axial load is present to hold them in axial alignment with the tubular cannula 42.

Figure 13:
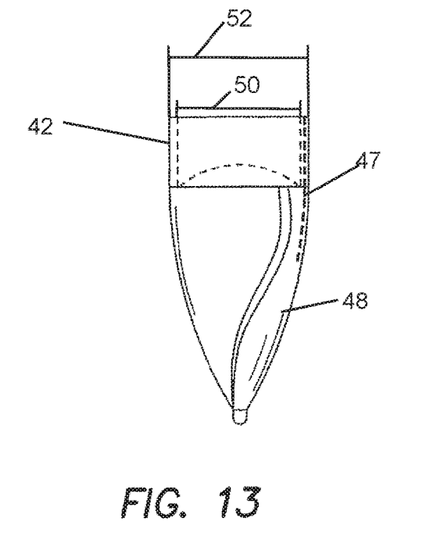
FIG. 13 is a side-section view of a tissue separating distal cannula portion in accordance with another embodiment of the invention having a hinge member and a centering portion.
Figure 14:
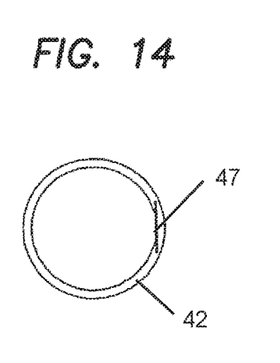
FIG. 14 is an end view of the tissue separating distal cannula portion of FIG. 13.
Figure 15:
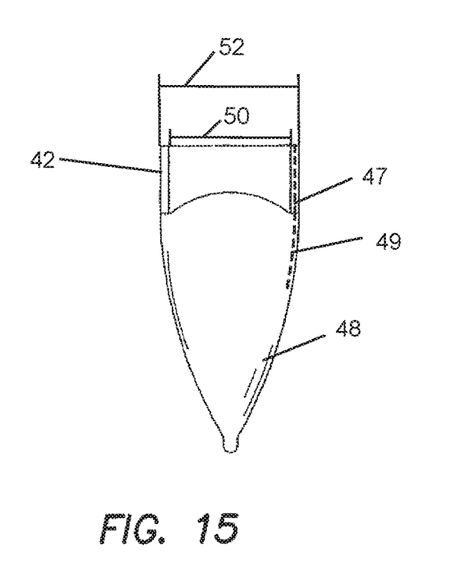
FIG. 15 is a side-section view of a distal cannula portion having a centering portion in accordance with another embodiment of the invention.
Figure 16:
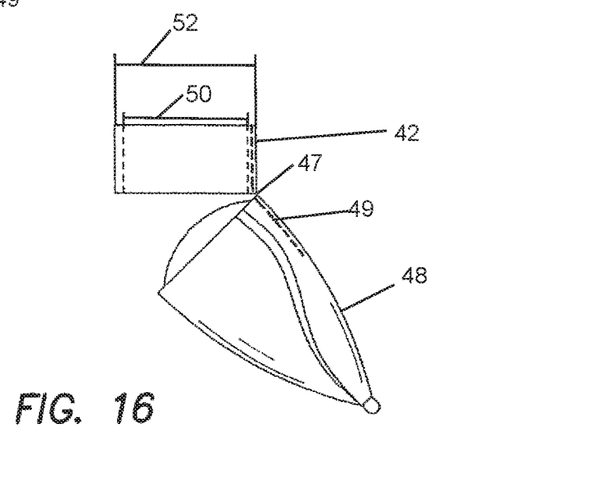
FIG. 16 is a side-section view of the tissue separating distal cannula portion of FIG. 13 in a partial retention condition.

A biased condition may be achieved using a spring, spring wire, offset hinge or a plastic "living" hinge. Considering the thin-wall nature of the cannula itself, a substantially flat ribbon of metal may comprise a preferred embodiment in the present invention where the ribbon is insert molded or fitted into the wall of the cannula 42 radially between an inner diameter 50 and an outer diameter 52 and subsequently inserted into a slot 49 in the distal tip 48. (FIGS. 13, 15-16). The ribbon may be configured to bias the distal tip in either the axial or off-axis condition or both. A detent or over-center configuration may be achieved by forming the hinge-ribbon into a cross sectional semi-circle to match the cross section of the cannula tube. The semi-circular cross section of the ribbon results in a "snap-over" or "click" that places the tip in axial alignment or, alternately, out of axial alignment upon urging from an included instrument. A rounded or tapered proximally facing extension upon the proximal end of the distal tip that is sized and configured to fit or "nest" into the distal end of the cannula tube assures correct axial alignment of the tip and the cannula.

Figure 17:
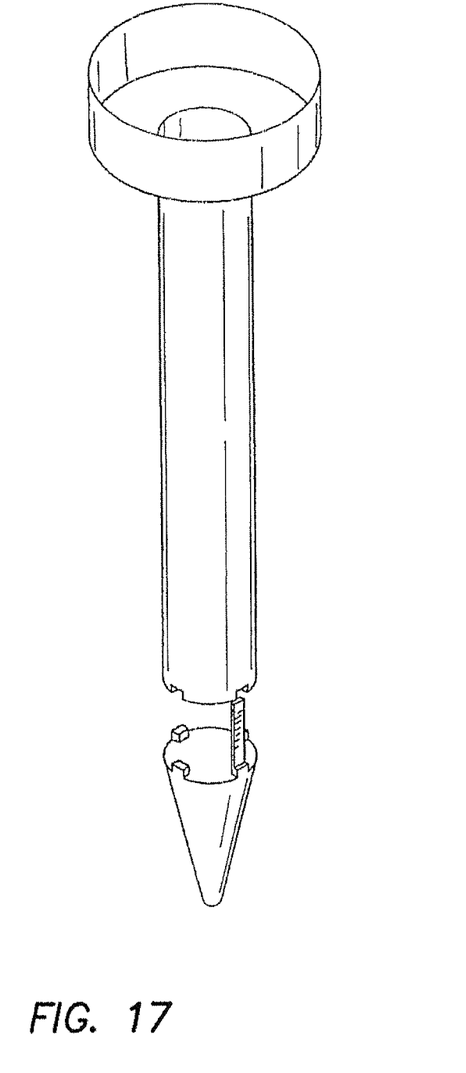
FIG. 17 is a perspective exploded view of a cannula in accordance with another embodiment of the invention, illustrating the placement of a spring-hinge in a solid distal tip.
Figure 18:
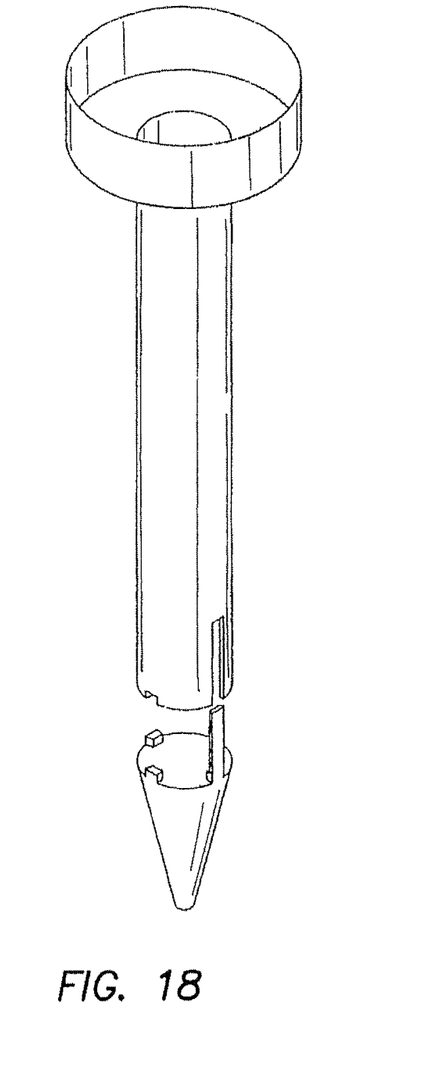
FIG. 18 is a perspective exploded view of a cannula in accordance with another embodiment of the invention, illustrating the placement of a spring-hinge in the cannula wall.
Figure 19:
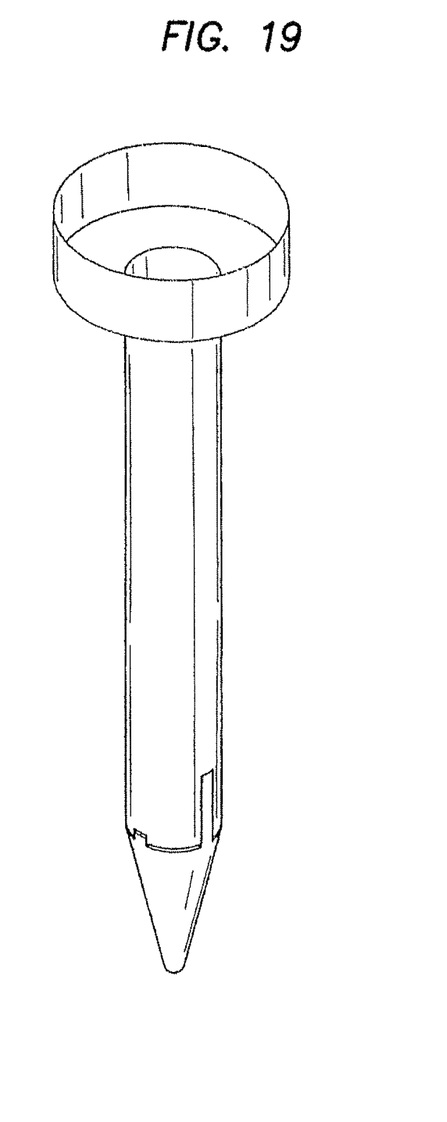
FIG. 19 is a perspective view of the cannula of FIG. 18 with the spring-hinge being placed in the cannula wall.

Referring to FIGS. 17-19, there is shown another aspect of the present invention including alignment features associated with the distal tip and the cannula tube. Proximally facing extensions associated with the tip fit into distally facing slots or features associated with the distal end of the cannula. These features allow the assembly to be twisted without challenging the retention member.

It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:

1. A laparoscopic surgical access port system comprising:
  a trocar cannula comprising an elongate thin-walled tubular body having a proximal end and a distal end and a longitudinal axis extending between the proximal end and the distal end, the elongate tubular body having an inner diameter, an outer diameter, and comprising a lumen disposed radially inwardly of the inner diameter, the lumen extending longitudinally between the proximal end and the distal end, the lumen sized and configured to receive laparoscopic surgical instruments;

a tissue-separating distal tip member pivotably coupled to the trocar cannula at the distal end, the distal tip member comprising a slot formed therein, and the distal tip member movable from a first position aligned with the longitudinal axis to a second position to one side off axis from the longitudinal axis; and a retention member fitted into the wall of the tubular body of the trocar cannula at the distal end radially between the inner diameter and the outer diameter and extending into the slot in the distal tip member.

2. The laparoscopic surgical access port system of claim 1, further comprising a seal housing operably connected to the proximal end of the trocar cannula.

3. The laparoscopic surgical access port system of claim 1, wherein the retention member comprises a flat ribbon.

4. The laparoscopic surgical access port system of claim 3, wherein the retention member is biased to maintain the distal tip member in the first position.

5. The laparoscopic surgical access port system of claim 3, wherein the retention member is biased to maintain the distal tip member in the second position.

6. The laparoscopic surgical access port system of claim 3, wherein the retention member has a detent configuration to position the distal tip member stably in one of the first position and the second position.

7. The laparoscopic surgical access port system of claim 1, wherein the retention member has a curved cross-sectional profile.

8. The laparoscopic surgical access port system of claim 1, wherein the distal tip member comprises a rounded proximally facing extension sized and configured to nest into the distal end of the trocar cannula.

9. The laparoscopic surgical access port system of claim 1, wherein the distal tip member comprises a single-piece tip.

10. The laparoscopic surgical access port system of claim 1, wherein the retention member extends distally of the distal end of the cannula into the slot in the distal tip member.

11. A laparoscopic surgical access port system for placement through a body wall comprising:

a trocar cannula comprising an elongate tubular body having a proximal end and a distal end and a longitudinal axis extending between the proximal end and the distal end, the elongate tubular body comprising a lumen extending longitudinally between the proximal end and the distal end, the lumen sized and configured to receive laparoscopic surgical instruments; and a single-piece tip member pivotably connected to the trocar cannula at the distal end, the tip member sized and configured to separate body tissue and guide the elongate tubular body through the body wall, the tip member comprising a hollow member sized and configured to receive a specimen therein;

wherein the single-piece tip member is pivotable from a first position substantially blocking the lumen at the distal end of the elongate tubular body and aligned with the longitudinal axis to a second position off axis with the longitudinal axis; and wherein the tip member automatically realigns with the longitudinal axis as the trocar cannula is withdrawn from the body wall.

12. The laparoscopic surgical access port system of claim 11, further comprising a seal housing operably connected to the proximal end of the trocar cannula.

13. The laparoscopic surgical access port system of claim 11, wherein the tip member has a substantially blunt dilating exterior surface.

14. The laparoscopic surgical access port system of claim 11, wherein the tip member is biased to the second position.

15. The laparoscopic surgical access port system of claim 11, wherein the single-piece tip member has an over-center pivot configuration such that the single-piece tip member is alternately positionable in the first position and the second position.

16. The laparoscopic surgical access port system of claim 15, further comprising a substantially flat metal ribbon pivotably connecting the single-piece tip member to the trocar cannula, the metal ribbon configured to provide the over-center pivot.

* * * * *